(12) United States Patent
Dadd et al.

(10) Patent No.: US 7,349,744 B2
(45) Date of Patent: Mar. 25, 2008

(54) COCHLEAR ELECTRODE ARRAY

(75) Inventors: Fysh Dadd, Lane Cove (AU); Claudiu Treaba, Englewood, CO (US)

(73) Assignee: Cochlear Limited, Lane Cove, NSW (AU)

( * ) Notice: Subject to any disclaimer, the term of this patent is extended or adjusted under 35 U.S.C. 154(b) by 190 days.

(21) Appl. No.: 10/825,360

(22) Filed: Apr. 16, 2004

(65) Prior Publication Data

US 2004/0236390 A1    Nov. 25, 2004

(30) Foreign Application Priority Data

Apr. 16, 2003    (AU) .............................. 2003901852

(51) Int. Cl.
*A61N 1/00*    (2006.01)

(52) U.S. Cl. ..................................... 607/137

(58) Field of Classification Search ................. 607/137
See application file for complete search history.

(56) References Cited

U.S. PATENT DOCUMENTS

| | | | |
|---|---|---|---|
| 4,898,183 A | 2/1990 | Kuzma | |
| 5,443,493 A | 8/1995 | Byers et al. | |
| 6,078,841 A * | 6/2000 | Kuzma | 607/137 |
| 6,096,059 A | 8/2000 | Kuzma | |
| 6,119,044 A * | 9/2000 | Kuzma | 607/137 |
| 6,321,125 B1 * | 11/2001 | Kuzma | 607/137 |
| 7,063,708 B2 * | 6/2006 | Gibson et al. | 606/129 |
| 2003/0069613 A1 | 4/2003 | Kuzma et al. | |

FOREIGN PATENT DOCUMENTS

WO    WO 03/070133    8/2003

\* cited by examiner

*Primary Examiner*—Carl Layno
*Assistant Examiner*—Brian T. Gedeon
(74) *Attorney, Agent, or Firm*—Connolly Bove Lodge & Hutz LLP

(57) ABSTRACT

An implantable tissue-stimulating prosthesis such as a cochlear implant system comprising an elongate carrier member having a distal end, a proximal end, and at least one electrode positioned thereon; at least one electrical conductor extending from one or more of the at least one electrode; a lead extending from the carrier member and enclosing the at least one electrical conductor; and a holding member constructed and arranged to radially extend outwardly from the surface of the carrier member to facilitate grasping of the holding member during implantation of the carrier member in a patient.

29 Claims, 4 Drawing Sheets

COCHLEAR ELECTRODE ARRAY

CROSS-REFERENCE TO RELATED APPLICATIONS

This application claims the priority of Australian Provisional Patent Application No. 2003901852, entitled "Cochlear electrode array," filed on Apr. 16, 2003. The entire disclosures and contents of the above application are hereby incorporated by reference. This application is related to International Application No. PCT/AU03/00229 and U.S. Pat. Nos. 4,532,930, 6,537,200, 6,565,503, 6,575,894, and 6,697,674. The entire disclosure and contents of the above applications are hereby incorporated by reference.

BACKGROUND

1. Field of the Invention

The present invention relates generally to a tissue-stimulating prosthesis and, more particularly, to an electrode carrier member for such a prosthesis.

2. Related Art

Delivery of electrical stimulation to appropriate locations within the body may be used for a variety of purposes. For example, function electrical stimulation (FES) systems may be used to deliver electrical pulses to certain muscles of a recipient to cause a controlled movement of the limb of such a recipient.

As another example, electrical stimulation of the cochlea using cochlear implant systems may also be used to directly deliver electrical stimulation to the auditory nerve fibers, thereby allowing the brain to perceive a hearing sensation resembling the natural hearing sensation normally delivered to the auditory nerve.

Cochlear implant systems typically have two primary components: an external component commonly referred to as a control unit, and an implanted component commonly reffered to as a receiver/stimulator unit. Traditionally, both of these components cooperate with each other together to provide the sound sensation to a recipient.

The external component has traditionally included a microphone that detects sounds, such as speech and environmental sounds, a speech processor that selects and converts certain detected sounds, particularly speech, into a coded signal, a power source such as a battery, and an external transmitter antenna.

The coded signal output by the speech processor is transmitted transcutaneously to the implanted receiver/stimulator unit located within a recess of the temporal bone of the recipient. This transcutaneous transmission occurs via the external transmitter antenna which is positioned to communicate with an implanted receiver antenna provided with the receiver/stimlator unit. This communication transmits the coded sound signal while also providing power to the implanted receiver/stimulator unit. Conventionally, this link has been in the form of a radio frequency (RF) link, but other such links have been proposed and implemented with varying degrees of success.

The implanted receiver/stimulator unit traditionally includes the noted receiver antenna that receives the coded signal and power from the external processor component. The implanted unit also includes a stimulator that processes the coded signal and outputs a stimulation signal to an intracochlear electrode assembly mounted to a carrier member which applies the electrical stimulation directly to the auditory nerve producing a hearing sensation corresponding to the original detected sound.

To position the carrier member that is mounting the electrode assembly, a surgeon typically forms a cochleostomy before gripping the member by hand or with a tool and then inserting a leading end of the carrier member through the cochleostomy and into preferably the scala tympani of the cochlea.

One potential problem during the insertion process is the potential for the carrier member to be damaged and/or rendered at least partially inoperative due to the handling the member receives prior to and during the insertion procedure.

SUMMARY

In one aspect of the invention, an implantable tissue-stimulating prosthesis is disclosed. The prosthesis comprises: an elongate carrier member having a distal end, a proximal end, and at least one electrode positioned thereon; at least one electrical conductor extending from one or more of the at least one electrode; a lead extending from the carrier member and enclosing the at least one electrical conductor; and a holding member constructed and arranged to radially extend outwardly from the surface of the carrier member to facilitate grasping of the holding member during implantation of the carrier member in a patient.

In another aspect of the invention, a cochlear implant system is disclosed. The cochlear implant system comprises: a stimulator unit; an elongate carrier member having a distal end, a proximal end, and a multichannel electrode array positioned at the distal end thereof for implantation in the cochlear of a person; a plurality of electrical conduction means electrically coupling each electrode of the electrode array to the stimulator unit; and a holding member constructed and arranged to radially extend outwardly from the surface of the carrier member.

In a further aspect of the invention, a carrier member for use in a tissue-stimulating prosthesis is disclosed. The carrier member comprises: an elongate carrier member body having a distal end, a proximal end and a holding member radially extending outwardly from the surface of the carrier member body; an electrode array disposed at the distal end of the carrier member body; and means for communicating signals from a stimulator unit to the electrode array.

In a still further aspect of the invention, a method of implanting a tissue-stimulating prosthesis in a desired location in a recipient is disclosed. The method comprises: providing an elongate carrier member comprising a holding member extending from a surface thereof, electrodes disposed at a distal end thereof, and electrical conductors connected to the electrodes and extending through the carrier member from the distal to proximal end thereof; forming a cochleostomy, gripping the holding member; and inserting a substantially straight carrier member through the cochleostomy and into the cochlea.

DETAILED DESCRIPTION

Embodiments of the present invention are directed to an apparatus and method for facilitating implantation of a medical device into a patient. Embodiments of the present invention are described below in connection with one type of medical device, a cochlear prosthetic device. Cochlear prostheses use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear prosthetic device provides stimulation of the cochlear nucleus in the brainstem.

Exemplary cochlear prostheses in which the present invention may be implemented include, but are not limited to, those systems described in U.S. Pat. Nos. 4,532,930, 6,537,200, 6,565,503, 6,575,894 and 6,697,674, the entire contents and disclosures of which are hereby incorporated by reference herein. As described therein, cochlear prostheses generally include an external, wearable control unit that determines a pattern of electrical stimulation that is provided to an implanted stimulator unit containing active circuitry in a hermetic enclosure. Electrical stimulation channels are routed through electrodes to provide electrical stimulation of auditory nerve cells.

Figure 1:
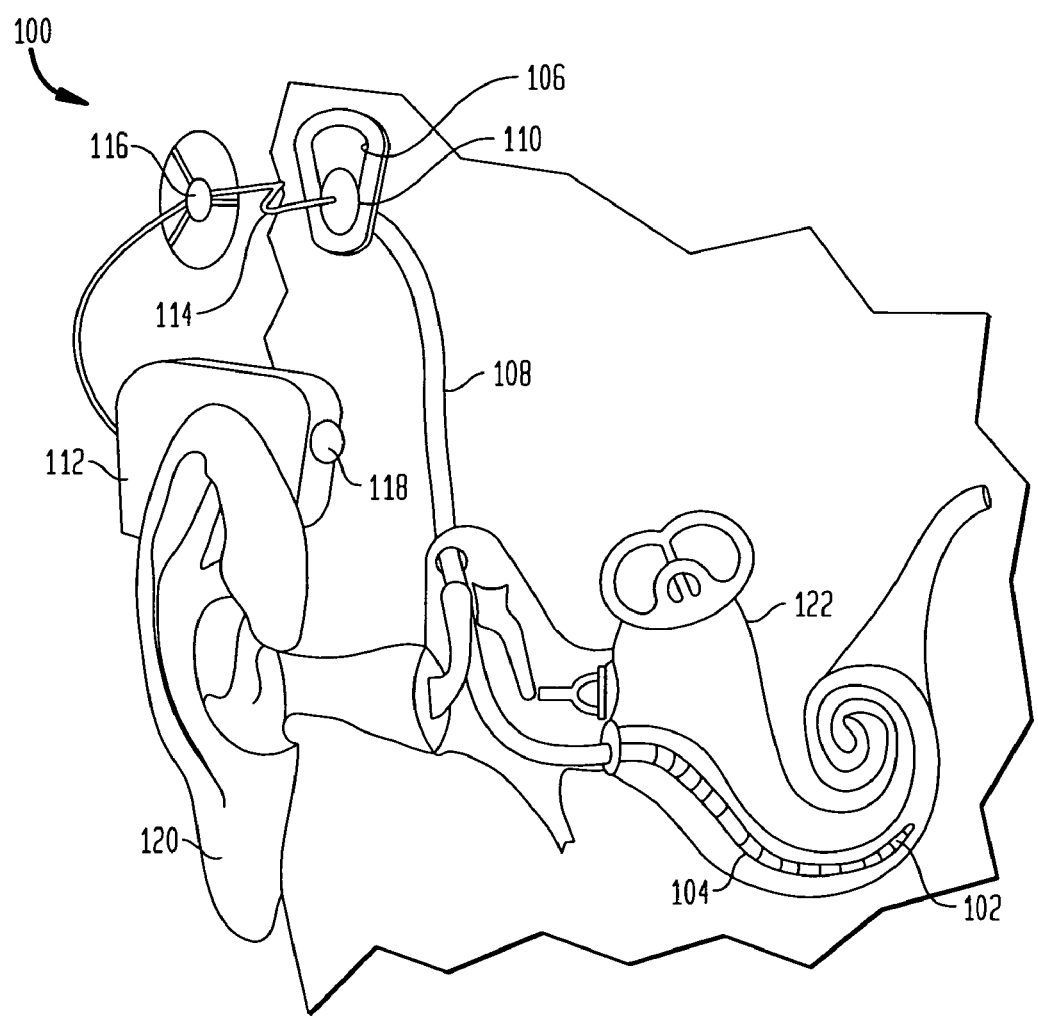
FIG. 1 is a block diagram of an exemplary cochlear implant system suitable for implementing embodiments of the present invention.

FIG. 1 is a schematic diagram of an exemplary cochlear implant system or prosthetic device 100 in which embodiments of the present invention may be implemented. In the context of such an application, embodiments of the present invention are directed to a carrier member of an electrode array 104 which has a holding member disposed on the surface thereof for the surgeon to grasp during insertion or implantation of the electrode array into the cochlear 122 of a recipient (also referred to herein as a patient).

Once implanted, electrodes 102 of the electrode array 104 receive stimulation signals from a stimulator unit 106. Stimulator unit 106 is typically electrically connected to electrode array 104 by way of electrical lead 108. Lead 108 is preferably continuous with no electrical connectors external the housing of stimulator unit 106.

Stimulator unit 106 is preferably positioned within a housing that is implantable within the patient. The housing for stimulator unit 106 is typically implantable within a recess in the bone behind the ear posterior to the mastoid. When implanted, the housing preferably contains, in addition to stimulator unit 106, a receiver unit 110. Receiver unit 110 is preferably adapted to receive signals 114 from a controller 112. Controller 112 is, in use, preferably mounted external to the body behind the outer ear 120 of the patient such that signals 114 are transmitted transcutaneously through the skin of the patient.

Signals 114 travel from controller 112 to receiver unit 110 and vice versa. Receiver unit 110 includes a receiver antenna, such as an antenna coil, adapted to receive radio frequency (RF) signals from a corresponding transmitter antenna 116, such as an antenna coil, worn externally of the body. The radio frequency signals may comprise frequency modulated (FM) signals. It should be appreciated that the receiver antenna may also transmit signals, and that the transmitter antenna may receive such signals. The transmitter antenna coil is preferably held in position adjacent the implanted location of the receiver antenna coil by way of respective attractive magnets (not shown) mounted centrally in, or at some other position relative to, the coils.

External controller 112 comprises a speech processor (not shown) adapted to receive signals output by a microphone 118. During use, microphone 118 is preferably worn on the pinna of the recipient, however, other suitable locations may be envisaged, such as a lapel of the recipient's clothing. The speech processor encodes the sound detected by microphone 118 into a sequence of electrical stimuli in accordance with speech coding stratagies now or later developed for cochlear implant systems. The encoded sequence is transferred to the implanted receiver/stimulator unit using the transmitter and receiver antennae. The implanted receiver/stimulator unit demodulates the signals and allocates the electrical pulses to the appropriate electrode 102 by an algorithm which is consistent with the chosen speech coding strategy.

External controller 112 may further comprise a power supply (not shown). The power supply may comprise one or more rechargeable batteries. The transmitter and receiver antennae are used to provide power via transcutaneous induction to the implanted reciever/stimulator unit and the electrode array.

While cochlear implant system 100 is described as having external components, in another embodiment, the controller, including the microphone, speech processor and power supply may also be implantable. In such embodiments, the controller may be contained within a hermetically sealed housing or the housing used for stimulator unit 106.

It should be appreciated that although embodiments of the present invention are described herein in connection with cochlear prosthetic device 100, the same or other embodiments of the present invention may be implemented in other tissue-stimulating prosthetic devices as well. Examples of such devices include, but are not limited to, other sensory prosthetic devices, neural prosthetic devices, and functional electrical stimulation (FES) systems. In sensory prostheses, information is collected by electronic sensors and delivered directly to the nervous system by electrical stimulation of pathways in or leading to the parts of the brain that normally process a given sensory modality. Neural prostheses are clinical applications of neural control interfaces whereby information is exchanged between neural and electronic circuits. FES devices are used to directly stimulate tissue having contractile cells to produce a controlled contraction of the same.

Figure 2:
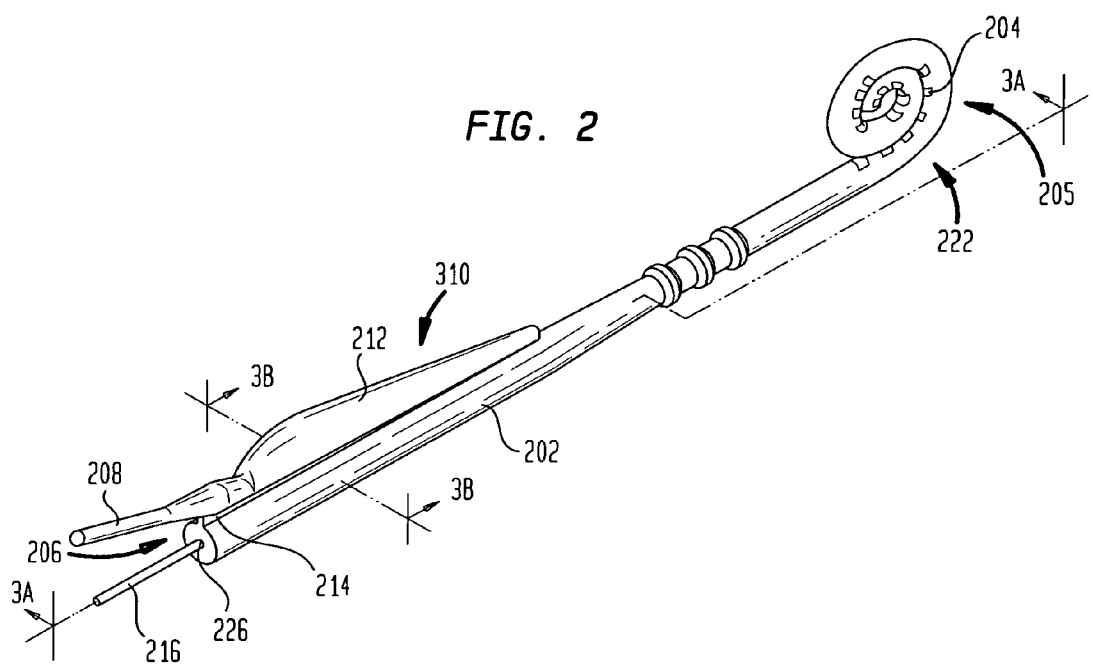
FIG. 2 is a perspective view of one embodiment of a carrier member according to the present invention.
Figure 3A:
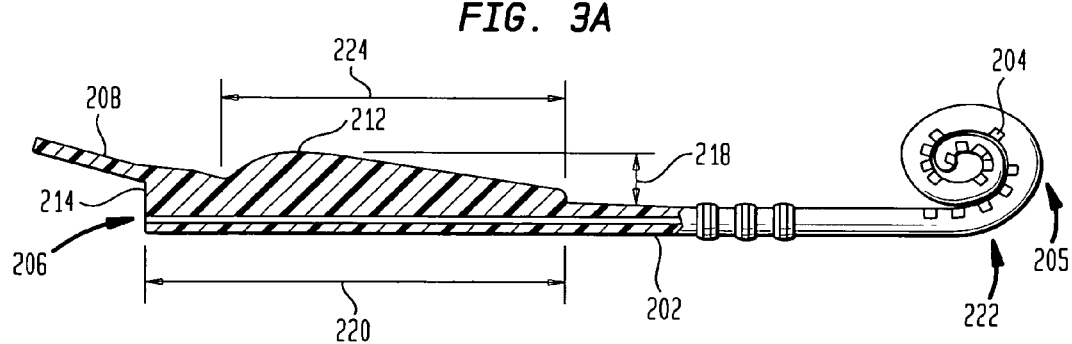
FIG. 3A is longitudinal a cross-sectional view of the carrier member illustrated in FIG. 2.
Figure 3B:
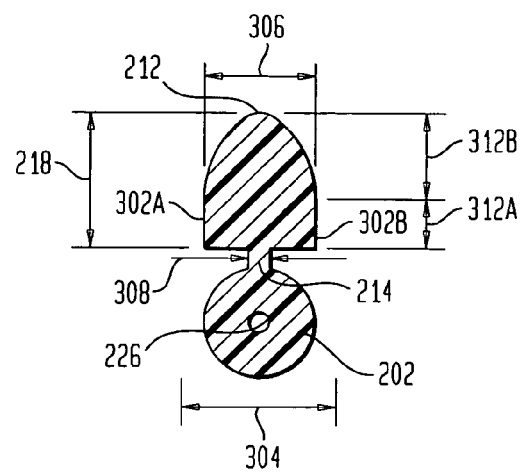
FIG. 3B is a lateral cross-sectional view of the carrier member illustrated in FIG. 2.

FIG. 2 is a perspective view of a carrier member 200 in accordance with one embodiment of the present invention. FIG. 3A is a longitudinal cross-sectional view of the carrier member shown in FIG. 2 taken along sectional line 3A-3A. FIG. 3B is a lateral cross-sectional view of the carrier member shown in FIG. 2 taken along sectional line 3B-3B. Carrier member 200, as noted, may be a component of a cochlear implant system such as cochlear implant system 100 illustrated in FIG. 1.

Carrier member 200 has an elongate body 202 having a proximal end 206 and a distal end 222. At least one electrode 204 is mounted or otherwise positioned at distal end 222 of carrier member body 202. In FIG. 2, a plurality of electrodes 204 is disposed on carrier member 202 to form an electrode array 205. In one embodiment, electrodes 204 are arranged in a longitudinal array. An electrical connection is made between electrodes 204 and stimulator unit 106 (FIG. 1) through lead 208 that extends out of carrier member body 202 near its proximal end 206. Lead 208 encloses at least one electrical conductor extending from each electrode 204 to stimulate unit 106. Such conductors, which are typically in the form of wires, are preferably formed from a suitable electrically-conducting metal. Preferably, the conductors are formed from a suitable biocompatible electrically-conducting material. It should be appreciated that other suitable electrically-conductive materials for use as conductive pathways through carrier member 200 may be used. For example, in alternative embodiments, semi-conducting materials and electrically-conducting polymers are used.

Disposed on an exterior surface of carrier member body 202 is a holding member 212. Holding member 212 extends radially outward from the exterior surface of carrier member body 202 and is configured to be held, grasped or otherwise utilized to control carrier member 200 during placement of the carrier member in a recipient.

In this illustrative embodiment, holding member 212 extends longitudinally along a region of carrier member body 202. In one embodiment, holding member 212 is positioned near proximal end 206 of carrier member body 202. It should be appreciated, however, that holding member 212 may be positioned at other locations on carrier member body 202. For example, in one alternative embodiment, holding member 212 is positioned closer to distal end 222 of carrier member 200.

Holding member 212 extends outwardly for a distance 218 defining the height of the holding member. In one embodiment, height 218 of holding member 212 is slightly greater than width 304 (FIG. 3B) of carrier member body 202. It should be appreciated, however, that height 218 of holding member 212 may vary along the length of holding member 212, with the variable height defining regions of holding member 212. It should further be appreciated that the height of each such region of holding member 212 may be less than, greater than, or approximately equal to width 304 of carrier member body 202.

As best shown in FIG. 3B, holding member 212 has two sidewalls 302A, 302B (collectively and generally referred to as side wall(s) 302). In the illustrative embodiment, the cross-sectional shape of holding member 212 has a region 3 12A in which sidewalls 302 are substantially parallel with each other. Holding member 212 tapers in width 306 for a portion of its height 218 away from body 202 of carrier member 200, defining a tapered region 312B. In one embodiment, vertical region 310A constitutes between about 20% and 80% of height 218 of holding member 212. In one preferred embodiment, vertical region 312A constitutes anywhere between about 40% and 60% of height 218 of holding member 212. In a further embodiment, vertical region 312A constitutes approximately 50% of height 218 of holding member 212. It should be appreciated by those of ordinary skill in the art that in such a region 312A, sidewalls 302 of holding member 212 may be substantially parallel or parallel.

As one of ordinary skill in the art would appreciate, holding member 212 may have a number of different cross-sectional shapes. For example, in one embodiment, along one or more longitudinal regions of holding member 212, width 306 is contoured or has other cross-sectional configurations to facilitate a particular objective such as facilitating a secure grasp of holding member 212 manually or with a particular instrument. In one embodiment, holding member 212 has a curved upper surface.

In one embodiment, carrier member 200 further comprises a support member 214 that connects holding member 212 to body 202 of carrier member 200. Support member 214 may be connected to holding member 214 and carrier member body 202 using any attachment means now or later developed. Alternatively, holding member 212, support member 214 and carrier member body 202 are unitary. Support member 214 is an elongate member having a length 220 that is approximately equal to the maximum length 224 of holding member 212. In the embodiment shown in FIGS. 2 and 3A, support member 214 is slightly longer than holding member 212 to support the connection of lead 208. Support member 214 has, in certain embodiments, a width 308 that is less than the maximum width 306 of holding member 212. It should be appreciated, however, that the dimensions and configuration of support member 214 may vary to satisfy the requirements of the application and/or user. In one embodiment, support member 214 acts as a support rail and functions in a manner described below.

In the embodiment shown in FIGS. 2, 3A and 3B, holding member 212 is formed integrally with body 202 of carrier member 200. In another embodiment, holding member 212 is formed separately to carrier member 200 and then joined to the carrier member. In a further embodiment, holding member 212 may be removably or non-removably joined to carrier member 200. In yet other embodiments, holding member 212 may be mounted to carrier member 200 such that the relative position and orientation of holding member 212 may be adjusted to accommodate particular users and applications. Such alternative embodiments are described below.

As depicted in FIGS. 2 and 3A, lead 208 extends from carrier member 200. As noted, lead 208 contains at least one connector that extends from electrodes 204 back through body 202 and then to stimulator unit 106. Lead 208 is positioned such that wires passing therethrough do not pass through holding member 212. As such, carrier member 200 may be controlled by grasped holding member 212 without risk of damaging the relatively fine wires that are passing through body 202 of carrier member 200 and into lead 208.

While the depicted holding member 212 is a solid member, the holding member could be at least partially hollow or filled with a substance that is different than the substance used to form sidewalls 302 of holding member 212. For example, in one embodiment holding member 212 has a cavity filled with air. Carrier member 200 may be formed from a suitable biocompatible material that has sufficient flexibility for the particular application. In one embodiment, the biocompatible material may be a silicone, such as a flexible silicone elastomer-Silastic. Silastic MDX 4-4210 is an example of one suitable silicone for use in the formation of the elongate member. In another embodiment, elongate carrier member 200 may be formed from a polyurethane or similar material.

Figure 4:
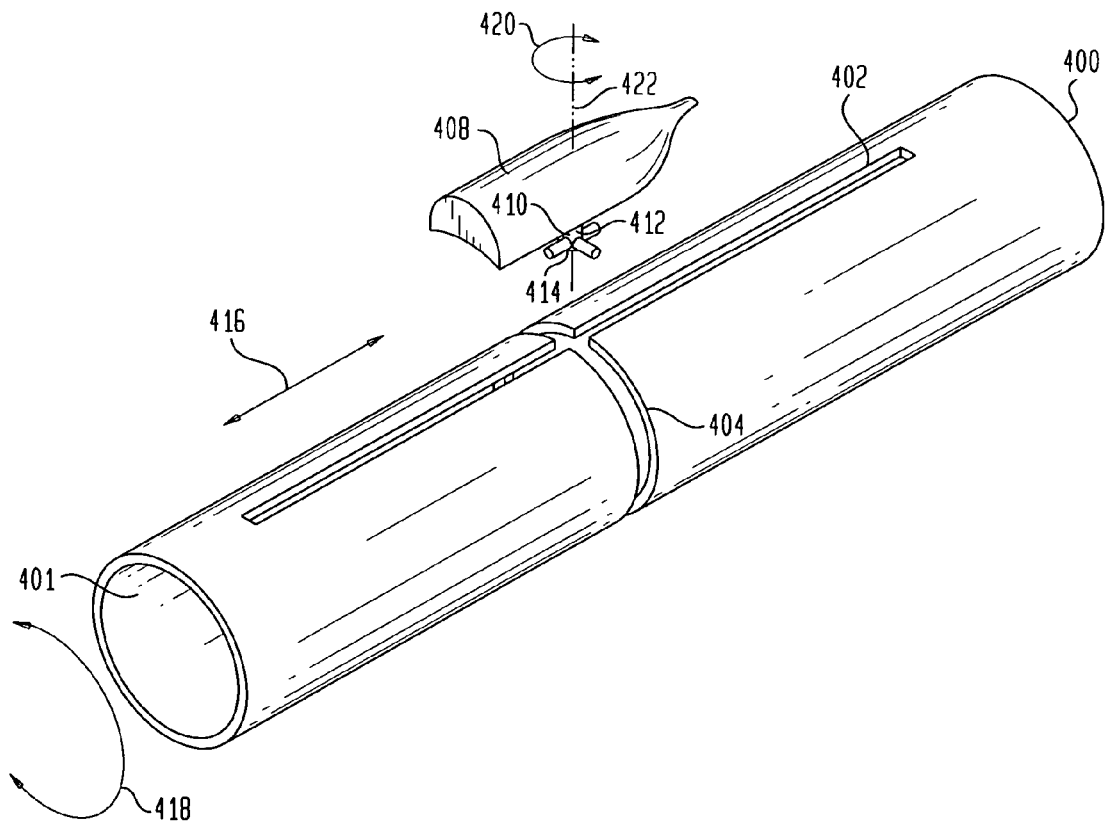
FIG. 4 is a perspective view of a carrier member implantation tube according to one embodiment of the present invention.

As noted, holding member 212 may be mounted to carrier member 200 such that the relative position and orientation of holding member 212 may be adjusted. Such embodiments are described next below in connection with the embodiments shown in FIG. 4. In the alternative embodiment illustrated in FIG. 4, a carrier member tube 400 is shown. In one embodiment, carrier member tube 400 has a lumen 401 configured to receive a conventional carrier member (not shown). In an alternative embodiment, carrier member tube 400 is the outer casing or housing of a carrier member.

Carrier member tube 400 has at least one slot 402 that extends substantially parallel to the longitudinal axis of carrier member body 202. Carrier member tube 400 may also have at least one slot 404 that extends laterally around the circumference of the tube. For ease of illustration and description, carrier tube 400 is shown to have one longitudinal slot 402 and one lateral slot 404. In this embodiment, a holding member 408 has an extension arm 410 with a shaft 412 and a retaining member 414 that releasably retains holding member 408 adjacent to tube 400 in slots 402, 404.

Specifically, extension arm 410 is adjustable to secure or release holding member 408 to tube 400. When extension arm 410 is in a position closest to holding member 408, retaining member 414 compresses the wall of tube 400 against holding member 408 to maintain holding member 408 in a stationary position during use. Conversely, when extension arm 410 is in a position farthest from holding member 408, retaining member 414 releases the wall of tube 400 enabling a user to reposition holding member 408 along longitudinal slot 402, as shown by arrow 416, and/or along lateral slot 404, as shown by arrow 418. In addition to adjusting holding member 408 to a desired location in slots 404, 402, holding member 408 may also be rotated to about an axis 422, as shown by arrow 420. In operation, holding member 212 may be translated around the circumferences of carrier member 200 to a desired position that suits the surgeon implanting the prosthesis. Still further, holding member 212 may be slidably mounted to carrier member 200 and so be adjustable in position along at least a portion of the length of the carrier member.

In this particular embodiment, holding member 408 may be removed from carrier member tube 400 by positioning holding member 408 at the intersection of longitudinal slot 402 and lateral slot 404, and aligning the extension arms of retaining member 414 with the slots 402 and 404.

It should be appreciated by those of ordinary skill in the art that the above adjustability, rotatability and removability of holding member 408 may be incorporated into the embodiments described above in connection with FIGS. 2 and 3A-3B. In one such embodiment, for example, tube 400 is the exterior wall of carrier member body 202. It should also be appreciated that any combination of one or more of these features may be implemented independently of each other.

As one of ordinary skill in the art would find apparent, techniques other than extension arm 410 may be implemented to releasably retain holding members 212, 408 to carrier member 200 or carrier member tube 400, respectively. For example, support member 214 may be configured to serve as a support rail that either extends through slots similar to slots 402, 404, or which is stationary and on which holding members 212, 408 are slidingly attached.

In accordance with one embodiment, holding member 212, 408 has some form of indicia that identifies the location of the holding member on carrier member 200 or carrier member tube 400. Such indicia, which may facilitate the implantation of a carrier member in the cochlea of a patient, is described below in connection with the embodiments described above in reference to FIGS. 2-3B. A surgeon using carrier member 200 may be informed by advice provided on the packaging or the like to note the position of holding member 212.

In one embodiment, the indicia may be the shape of holding member 212. For example, the shape of holding member 212 may be clearly different than the shape of the remainder of carrier member 200. In another embodiment, such indicia may be the color of at least a part of and preferably the entire surface of holding member 212. For example, the color of holding member 212 may be different than the color of carrier member body 202. In one specific embodiment, for example, holding member 212 is white in color whereas carrier member 200 may have a different color or indeed be essentially colorless due to the carrier member being formed from a translucent or transparent material, such as a silicone.

It should be appreciated by those of ordinary skill in the art that in certain embodiments that the color may be applied to holding member 212 or may be an inherent feature of the material selected to form the holding member. In one embodiment, a suitable filler, such as white titanium dioxide, may be mixed with a suitable silicone to form a holding member 212 that is approximately white in color.

In a still further embodiment, the indicia may include the tactility of holding member 212 in comparison to the tactility of the remainder of carrier member 200. This difference in feel may be achieved through various techniques now or later developed, such as the selection of a material that comprising at least part of holding member 212. For example, in one embodiment, holding member 212 is formed from a plastic material such as polypropylene while carrier member 200 is formed from a suitable biocompatible material such as silicone. In such an embodiment, holding member 212 will have a different tactility to that of a carrier member 200.

In another embodiment, the surface finish of holding member 212 may be different to that of the surface finish of carrier member 200. For example, undulations or channels formed in holding member 212 would present a different tactility to the normally relatively smooth finish of the surface of carrier member 200.

It will be appreciated that holding member 212 could have two or more of the noted indicia. For example, in at least one particular embodiment, holding member 212 could have both a different color and have a different tactility to that of carrier member 200.

Holding member 212 may be configured to be manipulated by either or both the fingers of a surgeon as well as by suitable surgical tools. Such tools include, but are not limited to, forceps or tweezers, hooks, clamps and suction tools, and others now or later developed. Such a configuration ensures that carrier member 200 may be used by any surgeon irrespective of whether that surgeon prefers to handle the carrier member by hand or with a tool during an implantation procedure. It should also be appreciated that the configuration of holding member 212 may be such that it is suitable for a particular application, surgical procedure, application and the like.

Figure 5:
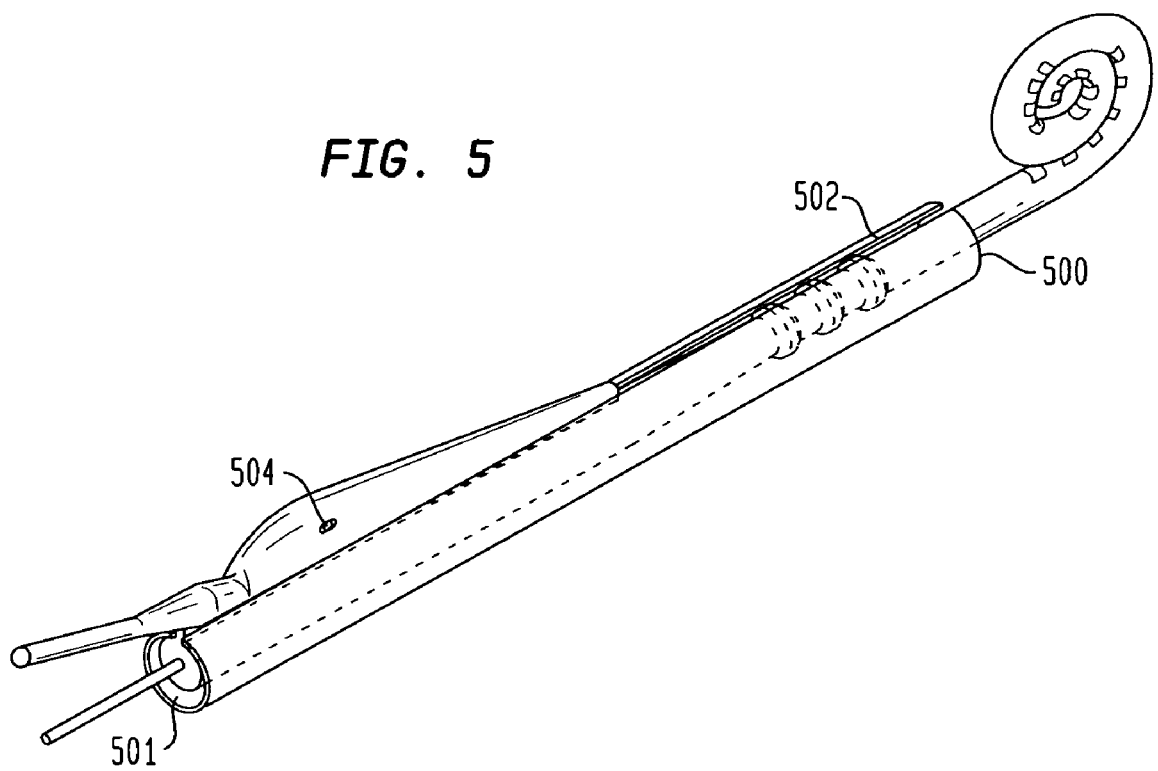
FIG. 5 is a perspective view of a insertion tool cartridge with the embodiment of the carrier member illustrated in FIG. 2 inserted therein.

Embodiments of the depicted carrier member 200 may also be insertable using an insertion tool (not shown). Such an insertion tool supports carrier member 200 and assists in delivering electrode array 205 of the carrier member to the insertion location. One insertion tool particularly well-suited for use with certain embodiments a carrier member of the present invention is described in International Application No PCT/AU03/00229, which is hereby incorporated by reference herein. Such embodiments of the present invention are directed to ensuring that the carrier member is shaped in such a manner where the carrier member may easily be adapted for use with such a tool. FIG. 5 is a perspective view of a insertion tool cartridge 500 of the above-noted insertion tool. In the embodiment illustrated in FIG. 5, support member 214 is configured to extend through a slot 502 in cartridge 500 when carrier member 200 is placed within the tool. Such an arrangement results in carrier member 200 being operatively installed in the insertion tool with support member 214 extending through slot 502, and the remaining portion of holding member 212 being located external to the cartridge. Such an embodiment facilitates the implantation of an electrode array 104 that is electrically connected to simulator unit 106 via lead 108 with no electrical connectors therebetween.

In certain embodiments, holding member 214 may have one or more features that facilitate the grasping of carrier member 200 during, for example, the insertion of stylet 216 in lumen 226, or the installation of carrier member 200 into cartridge 500. Such additional grasping tool interface features may include, for example, an aperture 504 extending laterally through holding member 214, a pair of opposing indentations on opposing sides of holding member 214, etc.

The implantation of a carrier member such as carrier member 200 is described next below. Carrier member body 202 is formed from a resiliently flexible material. Carrier member 200 has a substantially straight configuration prior to implantation or insertion through a cochleostomy. Following completion of implantation, carrier member 200 adopts a spirally curved configuration that matches the spiral nature of the scala tympani of the human cochlea. Carrier member 200 is preferably pre-formed with a spiral configuration and is then straightened either during manufacture and packaging of the device or prior to implantation.

As depicted in FIG. 2, carrier member 200 may receive a stiffening element such as stylet 216 that is adapted to bias body 202 of carrier member 200 into at least a substantially straight configuration prior to and during initial insertion of carrier member 200 through the cochleostomy. The implementing stiffening element is preferably formed from a non-bioresorbable material such as a metal or metallic alloy. For example, in one embodiment, stylet 216 is made of platinum.

Stylet 216 is received in a lumen 226 within body 202 of carrier member 200. Lumen 226 extends from an opening at proximate end 206 and extends through body 202 to a location proximate distal end 222 of carrier member 200. Preferably, lumen 226 does not extend through holding member 212. Stylet 216 may be positioned in lumen 226 during manufacture of carrier member 200 and serves to straighten carrier member 200 that would otherwise preferentially adopt a spirally curved configuration.

During use, distal end 222 of carrier member 200 is typically inserted into the cochlea through a cochleostomy and is inserted firstly towards the first basal turn of the cochlea. During this initial procedure, stylet 216 preferably remains within carrier member 200 and is also advanced into the cochlea. As such, there is preferably no relative movement of carrier member 200 to stylet 216 during insertion of the carrier member and up until distal end 222 is positioned at or near the first basal turn.

Once the surgeon has advanced the device to this position, stylet 216 is then held in place as carrier member 200 is held at its holding member 212 and then advanced relatively forwardly still further into the cochlea. As stylet 216 is held, the portion of carrier member 200 adjacent distal end 222 slides forwardly off stylet 216. As this occurs, that portion of carrier member 200 begins to adopt its preferential curved configuration, causing distal end 222 to move further into the spiral-shaped scala tympani of the cochlea, preferably without striking the wall of the basal turn of the cochlea.

Once the electrode array 205 has been advanced the desired distance into the cochlea, carrier member 200 may be held in place by holding holding member 212 as stylet 216 is withdrawn rearwardly out of lumen 226 and back out through the cochleostomy. By advancing carrier member 200 at least partially off stylet 216, the leading portion of carrier member 200 is free to start to adopt its preferential curved configuration and so enables the elongate carrier member to be inserted into the cochlea in a way which minimizes, and preferably eliminates, trauma to the walls of the cochlea.

On complete removal of stylet 216, elongate carrier member 200 is free to adopt the fully curved pre-formed orientation along at least part of its entire length and is so placed in its final position in the cochlea.

When implemented in connection with a cochlear prosthetic device, embodiments of the present invention assist a surgeon in performing a cochlear implantation by identifying which portion of carrier member 200 should be held during the implantation procedure if the potential for damage to the member is to be minimized. The reduction in potential for damage to the carrier member 200 should lead to an even lower rate of implant failure following implantation than hitherto has been the case.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All documents, patents, journal articles and other materials cited in the present application are hereby incorporated by reference. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An implantable tissue-stimulating prosthesis comprising:
   an elongate carrier member having a distal end, a proximal end, and at least one electrode positioned thereon;
   at least one electrical conductor extending from one or more of the at least one electrode;
   a lead extending from the carrier member and enclosing the at least one electrical conductor; and
   a holding member constructed and arranged to radially extend outwardly from the surface of the carrier member to facilitate grasping of the holding member during implantation of the carrier member in a patient, wherein a carrier member tube comprises one or more longitudinal and lateral slots on its surface, and wherein the holding member is mounted in the carrier member tube so as to be adjustable along the one or more longitudinal and lateral slots.

2. The prosthesis of claim 1, wherein the holding member is positioned adjacent to the proximal end of the carrier member.

3. The prosthesis of claim 1, wherein the holding member is an elongate member that extends longitudinally along a length of the carrier member.

4. The prosthesis of claim 1, wherein the carrier member has a width; and wherein the holding member extends outwardly from the carrier member surface for a distance defining a height of the holding member.

5. The prosthesis of claim 4, wherein the holding member has a width that tapers for a portion of its height away from the carrier member body.

6. The prosthesis of claim 1, wherein the holding member has a width that varies along its height to define vertical regions.

7. The prosthesis of claim 1, further comprising:
a support member that connects the holding member to the carrier member.

8. The prosthesis of claim 7, wherein the support member has a width that is less than a maximum width of the holding member.

9. The prosthesis of claim 1, wherein the holding member is removably joined to the carrier member.

10. The prosthesis of claim 1, wherein the holding member is rotatably mounted to the carrier member.

11. The prosthesis of claim 1, wherein the holding member further comprises:
an indicia that identifies the holding member on the carrier member.

12. The prosthesis of claim 1, wherein the holding member is constructed and arranged to be manipulated by the fingers of a surgeon.

13. The prosthesis of claim 1, wherein the holding member is constructed and arranged to be manipulated by a surgical tool.

14. The prosthesis of claim 1, wherein the tissue-stimulating prosthesis is a cochlear implant system.

15. An implantable tissue-stimulating prosthesis comprising:
an elongate carrier member having a distal end, a proximal end, and at least one electrode positioned thereon;
at least one electrical conductor extending from one or more of the at least one electrode;
a lead extending from the carrier member and enclosing the at least one electrical conductor; and
a holding member constructed and arranged to radially extend outwardly from the surface of the carrier member to facilitate grasping of the holding member during implantation of the carrier member in a patient, wherein the holding member further comprises an indicia that identifies the holding member on the carrier member.

16. The prosthesis of claim 15, wherein the indicia comprises tactility of the holding member.

17. The prosthesis of claim 15, wherein the indicia comprises a relative shape of the holding member and the carrier member.

18. The prosthesis of claim 15, wherein the indicia comprises a color of the holding member.

19. The prosthesis of claim 15, wherein the holding member is positioned adjacent to the proximal end of the carrier member.

20. The prosthesis of claim 15, wherein the holding member is an elongate member that extends longitudinally along a length of the carrier member.

21. The prosthesis of claim 15, wherein the carrier member has a width; and wherein the holding member extends outwardly from the carrier member surface for a distance defining a height of the holding member.

22. The prosthesis of claim 15, wherein the holding member has a width that varies along its height to define vertical regions.

23. The prosthesis of claim 15, further comprising:
a support member that connects the holding member to the carrier member.

24. The prosthesis of claim 15, wherein the holding member is removably joined to the carrier member.

25. The prosthesis of claim 15, wherein the holding member is rotatably mounted to the carrier member.

26. The prosthesis of claim 15, wherein a carrier member tube comprises one or more longitudinal and lateral slots on its surface, and wherein the holding member is mounted in the carrier member tube such that the holding member is adjustable along the one or more longitudinal and lateral slots.

27. The prosthesis of claim 15, wherein the holding member is constructed and arranged to be manipulated by the fingers of a surgeon.

28. The prosthesis of claim 15, wherein the holding member is constructed and arranged to be manipulated by a surgical tool.

29. The prosthesis of claim 15, wherein the tissue-stimulating prosthesis is a cochlear implant system.

* * * * *